United States Patent [19]
Faries, Jr. et al.

[11] Patent Number: 5,502,980
[45] Date of Patent: Apr. 2, 1996

[54] STERILE DRAPE FOR USE IN MAKING SURGICAL SLUSH

[75] Inventors: Durward I. Faries, Jr., McLean, Va.;
Bruce R. Heymann, Silver Spring, Md.; Mark Licata, Richmond, Va.

[73] Assignee: O. R. Solutions, Inc., Chantilly, Va.

[21] Appl. No.: 399,976

[22] Filed: Mar. 7, 1995

Related U.S. Application Data

[60] Continuation-in-part of Ser. No. 274,869, Jul. 14, 1994, Pat. No. 5,400,616, which is a division of Ser. No. 125,279, Sep. 23, 1993, Pat. No. 5,331,820.

[51] Int. Cl.⁶ ........................................................ F25C 1/00
[52] U.S. Cl. ................................................. 62/342; 128/849
[58] Field of Search ............................. 62/66, 340, 342, 62/68; 128/846, 849; 4/DIG. 18, 452, 484, 580, 655

[56] References Cited

U.S. PATENT DOCUMENTS

| | | |
|---|---|---|
| 4,393,659 | 7/1983 | Keyes et al. . |
| 4,474,016 | 10/1984 | Winchell . |
| 4,934,152 | 6/1990 | Templeton . |
| 5,163,299 | 11/1992 | Faries, Jr. et al. . |
| 5,174,306 | 12/1992 | Marshall . |
| 5,331,820 | 7/1994 | Faries et al. . |
| 5,333,326 | 8/1994 | Faries et al. . |
| 5,429,801 | 7/1995 | Faries, Jr. et al. . |

OTHER PUBLICATIONS

U.S. Pat. application Ser. No. 08/326,423, filed Oct. 20, 1994, "Sterile Drape for Use in Making Surgical Slush".

*Primary Examiner*—William E. Tapolcai

[57] ABSTRACT

A sterile drape assembly includes a sheet of sterile drape material bonded to a disk-like member. The drape establishes a sterile field atop a surgical slush machine and is conformable to a cooling basin to provide a drape container impervious to the sterile slush medium. The disk-like member is preferably bonded to the bottom of the drape container and is engageable by a movable member projecting into the basin. The movable member (e.g., a longitudinally reciprocable vertical shaft) moves the member and the drape to dislodge frozen pieces of the sterile medium that attach to the sides of the drape container.

10 Claims, 3 Drawing Sheets

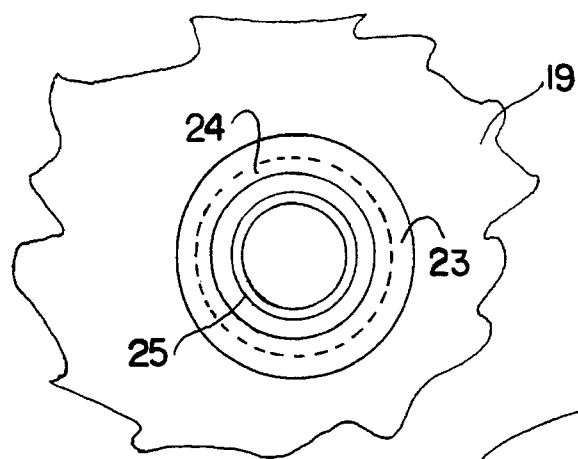
FIG. 4
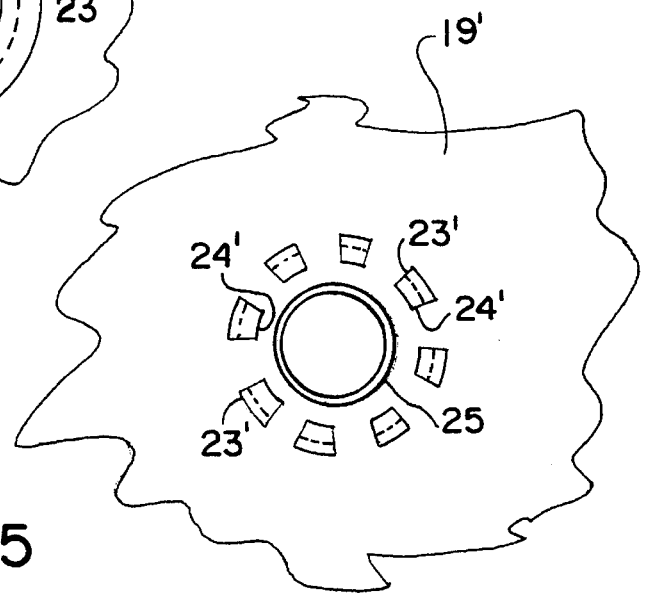
FIG. 5
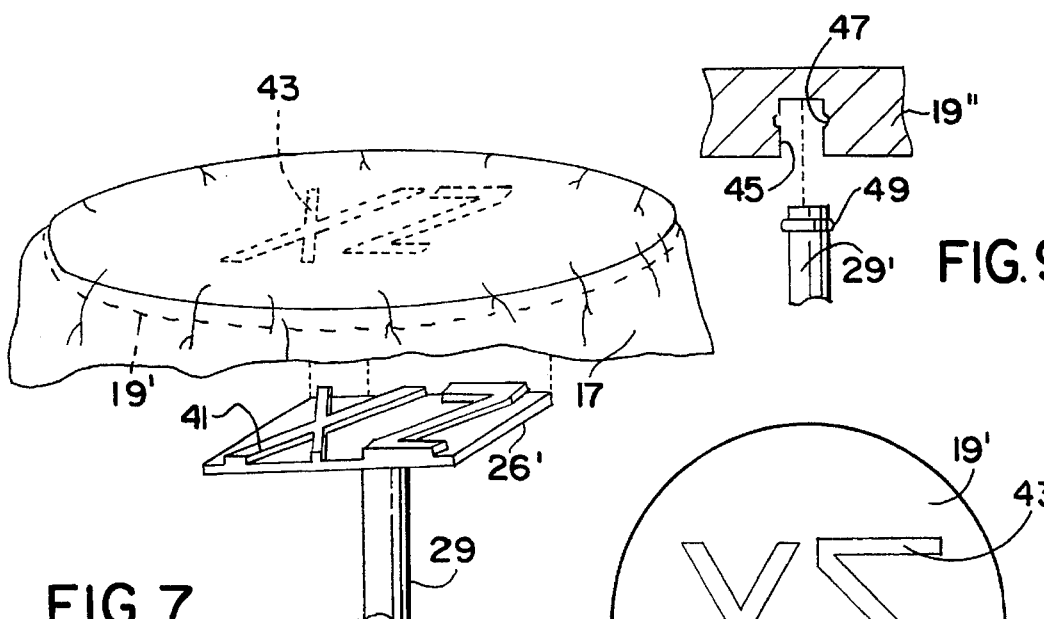
FIG. 7
FIG. 9
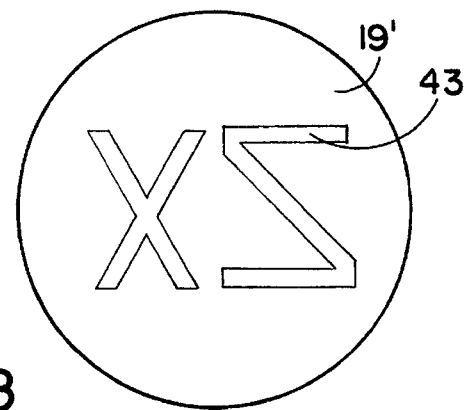
FIG. 8

1

STERILE DRAPE FOR USE IN MAKING SURGICAL SLUSH

CROSS-REFERENCE TO RELATED APPLICATIONS

This application is a continuation-in-part of our U.S. patent application Ser. No. 08/274,869, filed Jul. 14, 1994, which is a division of our U.S. Pat. No. 5,331,820.

BACKGROUND OF THE INVENTION

1. Technical Field

The present invention pertains to improvements in methods and apparatus for producing and collecting sterile surgical slush. In particular, the invention is an improvement of the methods and apparatus disclosed in our U.S. Patent No. 5,331,820 and the patents cited therein. The disclosures in those patents are expressly incorporated herein in their entireties.

2. Discussion of the Prior Art

Our aforesaid U.S. Pat. No. 5,331,820 addresses the problem of removing congealed frozen sterile medium from the sides of a sterile drape container in a surgical slush machine. Specifically, the sterile drape container is conformed to a cooled basin to establish a sterile field above the basin. The drape container collects a frozen sterile medium (e.g., saline) in a sterile slush-like consistency. The frozen medium tends to attach to the sides of the drape container in large clumps or pieces rather than automatically collecting within the container interior. Prior to the invention in the U.S. Pat. No. 5,331,820, operating room personnel attempted to detach frozen pieces from the drape container sides by scraping or impacting the pieces. This is highly undesirable since impacting and scraping can easily tear the drape and compromise the required sterile field. The 5,331,820 patent discloses a technique for automatically manipulating the drape relative to the basin wall to thereby cause the frozen congealed medium to detach from the drape sides and collect interiorly as the desired slush. Some of the embodiments disclosed in the patent cyclically move a plate or disk disposed between the drape and basin to manipulate the drape. The disk is described as being either secured to a movable machine or secured directly to the drape. It has been found that, for many applications, it is more convenient to have the plate or disk secured directly to the drape. Such an arrangement insures proper positioning of the drape in the cooling basin to effect automatic drape manipulation.

The present invention is concerned with optimizing the embodiment suggested in the aforesaid patent wherein the disk or plate is secured directly to the drape.

SUMMARY OF THE INVENTION

In accordance with the present invention a disk or plate is bonded by adhesive, welding, or the like to the underside of a sterile drape. The disk is provided with a fitting suitable for engaging a cyclically movable member to permit the disk to be cyclically moved in a manner to separate the drape container sides from the basin and cause frozen congealed pieces of sterile medium to fall into a slush pile. Depending upon the movable member, the plate may be rotated, wobbled or vertically reciprocated. In the preferred embodiment the plate is secured to the drape either by welding or by means of an adhesive capable of joining the disk and drape materials and withstanding temperatures over a range extending from below the freezing temperature of the sterile medium to above ambient temperatures typically encountered during storage and transportation of the drape and disk assembly. The sterile drape and disk thus comprise a complete sterile assembly that can be easily deployed on the surgical slush machine and then disposed of after a surgical procedure. Proper positioning of the drape relative to the basin and the sterile slush machine is assured since the plate must be connected to the movable member located in the basin.

These and other object, features and many of the attendant advantages of the present invention will be appreciated more readily as they become better understood from the following description considered in connection with the accompanying drawings wherein like parts in each of the several figures are identified by the same reference numerals.

BRIEF DESCRIPTION OF THE DRAWINGS

FIG. 4 is a bottom view in plan of a portion of the drape plate of FIG. 3.

FIG. 5 is a bottom view in plan of a portion of an alternative embodiment of the drape plate having a series of spaced wall increments forming an intermittent snap fit with the connector plate.

FIG. 7 is an exploded view in perspective of alternative apparatus for providing engagement between the movable mechanism and the disk drape assembly.

FIG. 8 is a bottom view in plan of the disk portion of the disk drape assembly of FIG. 7.

FIG. 9 is a detailed partial view in exploded elevation and partial section showing still another apparatus for providing engagement between the movable mechanism and the drape assembly.

DESCRIPTION OF THE PREFERRED EMBODIMENTS

Figure 2:
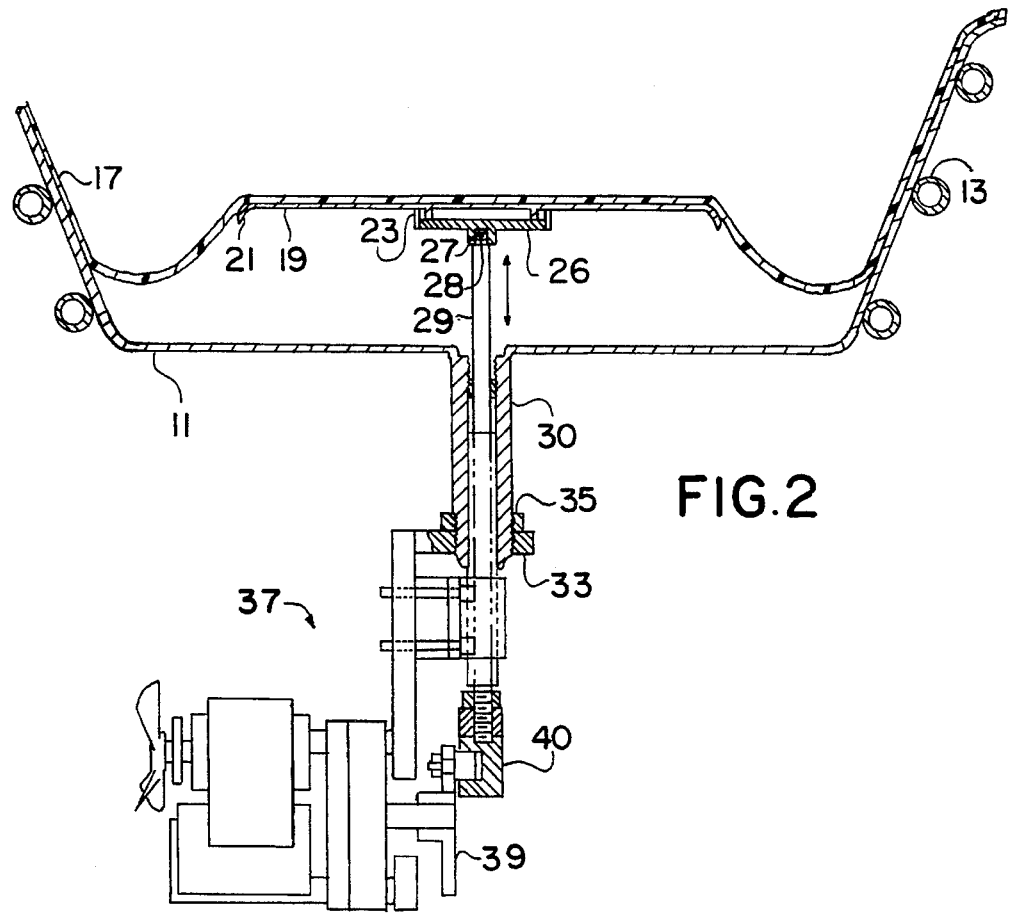
FIG. 2 is an elevational view in partial section showing one embodiment of the drape assembly of the present invention connected to an apparatus for manipulating the drape in a surgical slush machine.

Referring specifically to FIGS. 1–6 of the accompanying drawings, a surgical slush generating system of the type described in the above-referenced U.S. Pat. No. 5,331,820 includes a cabinet 10 with a top surface having a basin 11 mounted thereon in an appropriately sized recess. Although shown rounded with a circular rim, basin 11 may be oval, rectangular, square or any desired shape. Basin 11 is made of thermally conductive material, typically stainless steel, and includes a generally flat circular bottom wall and, in the illustrated embodiment, a generally frusto-conical sidewall. A conventional refrigeration unit is disposed within cabinet 10, it being noted that only the evaporator 13 of that unit is shown in FIG. 2. The refrigeration unit typically includes a compressor, a condenser and an expansion control unit connected by appropriate fluid conduits in a closed refrigeration loop with evaporator 13. The evaporator is in the form of coil wound about the exterior surface of basin 11 in thermal transfer relation therewith. When the refrigeration unit is activated by means of appropriate controls 15 on the top surface of cabinet 10, evaporator 13 cools the sidewall of the basin 11 to a temperature substantially below the freezing temperature of the sterile liquid used in forming the surgical slush. This temperature is preferably on the order of −30° F. to 10° F. For further details of the structure and operation of the refrigeration unit, reference is made to U.S. Pat. Nos. 4,393,659 (Keyes et al) and 4,934,152 (Templeton) incorporated herein by reference.

A sterile drape 17, preferably transparent, is disposed over the top and hangs down along the sides of cabinet 10, and is made to conform to the sidewall of basin 11. The portion of drape 17 disposed in the basin serves as a sterile receptacle for sterile liquid placed therein to be frozen to the desired sterile slush consistency. A disk or plate 19 is bonded to the drape at the underside of the receptacle portion and is configured to generally match the contour of the basin bottom while being supported, in a manner described below, slightly above the basin bottom between the drape and the basin. Typical sterile liquid used for this purpose is a 0.80% to 0.95% sodium chloride solution (i.e., saline). Drape 17 is made from a material that is impervious to the sterile liquid and sufficiently soft and flexible to conform to the basin sidewall. The drape may also have a preformed section contoured to match the basin sidewall. The thickness of the drape is preferably minimized to render thermal transfer therethrough most efficient, yet the thickness is sufficient to resist tearing and puncturing during normal use. Typically, and by way of example only, the drape may be made of materials commonly used in hospitals for drapes and has a thickness in the range of 3.0 to 10.0 mils. The drape and its adhered plate 19 are designed to be disposable after a single use (i.e., after a single surgical procedure) and are provided pre-sterilized and pre-packaged in a manner to preserve their sterile state during storage.

Figure 3:
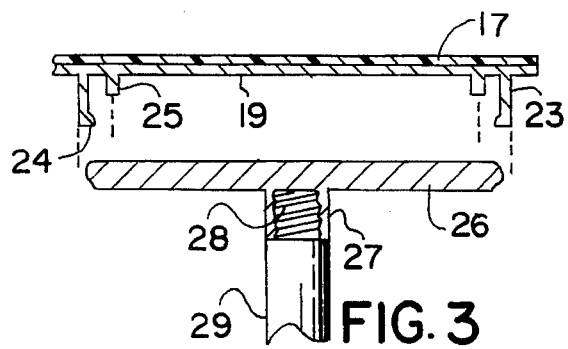
FIG. 3 is a exploded detailed view in partial section illustrating the manner in which the drape assembly of FIG. 2 is interconnected to the mechanism for manipulating the drape.

Disk or plate 19, in the embodiment illustrated in FIGS. 2–4 is generally circular with a short downturned annular lip 21 at its circumference. The downturned lip 21 is smoothly rounded to avoid sharp edges that might inadvertently tear drape 17 during movement of the drape. Disk 19 is permanently bonded to drape 17 (e.g., by means of a suitable adhesive 22) in flush abutment along the entire upper surface of the disk. Depending centrally from the bottom surface of disk 19 is an outer annular wall 23, shown in FIG. 4, having a short annular lip 24 extending radially inward from the wall bottom edge. An axially shorter annular wall 25 is spaced concentrically inward from wall 23 and likewise depends from the bottom surface of disk 19. Wall 23 is sufficiently resilient to permit a circular connector plate 26 to be received with a snap-fit engagement in the space bounded by wall 23. More particularly, plate 26 has a diameter slightly smaller than the diameter of the inside surface of annular wall 23 but slightly larger than the diameter of the annular inner edge of lip 24. Accordingly, when disk 19 is properly centered in basin 11 and pushed axially downward onto plate 26, the plate resiliently forces lip 24 upward and wall 23 outward until the plate axially passes the lip and its flat upper surface is stopped by the bottom annular edge of inner annular wall 25. Once plate 26 clears lip 24, the lip and wall 23 resiliently return to their unstressed position with lip 24 extending a short radial distance along the bottom surface of the plate. The plate is thusly engaged in a snap fit by the disk.

For use in basins having shapes other than circular, it is to be understood that drape plate 19 would be configured correspondingly, and, further, that connector plate 26 and lipped resilient wall 23 are not constrained to circular or annular shapes, respectively, but need only interact to form a secure snap fit attachment between drape plate 19 and reciprocation means described hereinafter. Moreover, resilient wall 23 and inwardly projecting lip 24 need not extend continuously around the perimeter of connector plate 26 but can, rather, consist of a series of separated spaced wall increments 23', as shown in FIG. 5, with corresponding lip increments 24' to form an intermittent snap fit between drape plate 19' and the perimeter of connector plate 26.

The bottom of plate 26 is provided with a centrally located downwardly depending hollow cylindrical stem 27. Stem 27 is interiorly threaded to receive the threaded tip 28 of the shaft 29 extending upwardly through the bottom of basin 11. In particular, the bottom of basin 11 is provided with a central hole communicating with a bore in an adapter tube 30 secured at its upper end to the bottom of basin 11 by any convenient means. The bottom end of adapter tube 30 is externally threaded and is engaged by a support bracket 33 and lock washer 35 such that bracket 33 is suspended interiorly of the machine cabinet (not shown in FIG. 2). A gear motor assembly, generally designated at 37, is supported by bracket 33 and includes a rotor 39 operatively engaged with a bearing track 40. Drive shaft 29 has its bottom end operatively engaged to bearing track 40 to cause the shaft to reciprocate longitudinally as rotor 39 rotates. Shaft 29 extends upwardly through adapter tube 30 and has its upper end secured to the center of the underside of plate 26 in the manner described above. Accordingly, as motor 37 reciprocates shaft 29 up and down, the shaft moves disk 19 up and down. The disk, in turn, moves the bottom of the drape container up and down to loosen pieces of frozen saline that form on the drape. The loosened pieces fall and collect in the center of the drape container as surgical slush.

Figure 1:
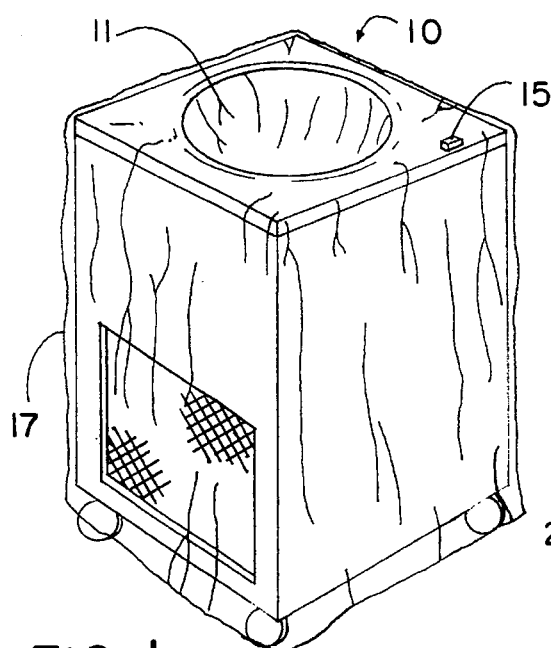
FIG. 1 is a view in perspective of a surgical slush machine of the type of which the present invention is employed.
Figure 6:
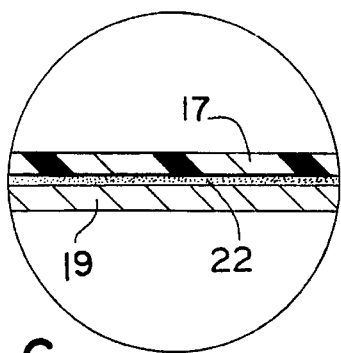
FIG. 6 is a detailed view of a portion of the drape assembly of FIG. 2.

As best illustrated in FIG. 6, drape 17 may be bonded to the flat top surface of disk 19 by means of a layer of adhesive substance 22. The preferred adhesive is hot melt acrylic, although other adhesive materials may be utilized, such as (without limitation) cyanoacrylate, UV-cure acrylate, epoxy, urethane, silicon, and the like. The drape and disk may also be bonded together by welding techniques such as radio-frequency welding, hot plate welding, ultrasonic welding, etc. The optimum adhesive or welding technique would, of course, depend upon the materials employed for the drape and disk. Typical drape materials are polyurethane, polyvinylchloride, thermoplastic olefins, polyethylene, polypropylene, copolymers of propylene and polyethylene. Importantly, the drape material must be impervious to the sterile medium (e.g., saline) from which the sterile slush is formed. Suitable materials for disk 19 include polycarbonate, acronitrile-butadiene-styrene copolymer, polymethylmethacrylate, rigid polyvinylchloride, rigid polyurethane, nylon, polyethylene, polystyrene and other rigid thermoplastics capable of being machined, thermoformed or injection molded to the desired shape.

Disk 19 must be sufficiently rigid to support the pile of surgical slush without bending, flexing or breaking. Typically, but without limitation, the disk is approximately three-quarters inch thick.

When the surgical slush machine is operating, the sterile liquid in the drape container freezes in pieces on the sidewalls of that container which is cooled by evaporator 13 through basin 11. As disk 19 moves up and down, the drape moves therewith, moving the drape container sidewalls alternately away and toward the basin walls. As the drape sidewalls are displaced relative to the basin sidewalls, the solid pieces of frozen sterile medium dissociate from the drape sidewall and fall into the central area of the drape container where slush is collected.

In deploying the drape assembly on the machine prior to a surgical procedure, plate 26 must first be independently attached to drive shaft 29 by threadedly engaging shaft tip 28 in stem 27 at the underside of the plate. In many instances plate 26 will already be secured to the drive shaft since the plate is located below the sterile field and need not be replaced for each procedure. The drape assembly is removed from its sterile package and positioned with the underside of disk 19 centered in basin 11 above plate 26. The disk is pushed downward until annular engagement wall 23 snaps onto and engages plate 26. The drape is thereby properly positioned as a drape container to be automatically manipulated by reciprocating drive shaft 29, whereby congealed sterile medium is automatically removed from the drape container sides.

The engagement between disk 19 and plate 26 need not be of the snap-fit type. For example, with reference to FIGS. 7 and 8, the reciprocating plate 26' may have a raised pattern 41 formed on its upper surface, and disk 19' may have a mating mirror image recessed pattern 43 defined in its bottom surface. Disk 19' can thus merely be placed atop plate 26' such that patterns 41 and 43 mutually engage; that is, raised pattern 41 is received in recessed pattern 43. In the disclosed embodiment, patterns 41, 43 represent meaningful indicia, such as alphanumeric characters, although any pattern configurations capable of engaging the plate and disk may be provided. It should also be noted that the raised pattern can be provided on the bottom surface of disk 19' to be received in a mirror image recessed pattern defined in the upper surface of plate 26'.

Another type of engagement between the drape disk and the reciprocating mechanism is illustrated in FIG. 9. Specifically, the underside of disk 19" is provided with an axial bore 45. The bore has an axially short, radially widened section 47 defined therein. The diameter of bore 45 is slightly larger than the diameter of drive shaft 26 which has a resilient ring 49 disposed circumferentially near its upper end. To engage disk 19" on shaft 29' it is only necessary to force the disk downward onto the vertical shaft until ring 49 is received in the radially widened section 47 of the bore where the ring becomes engaged in a snap-fit. The disk may be removed from such engagement by merely pulling the disk upward along with the drape after the surgical procedure is completed. It is to be noted that, in this embodiment, there is no need for a separate plate such as plates 26, 26' described above. It should be further noted that the snap-fit relationship between widened bore section 47 and ring 49 can be eliminated, in which case the drive shaft 29' would be received in bore 45 in a friction fit engagement.

From the foregoing it should be understood that the present invention does not depend on any particular engagement between the drape disk and the reciprocating mechanism; that is, it is only necessary to provide an engagement whereby the disk can be properly supported and reciprocated by the mechanism during the slush forming and maintaining procedure.

Figure 12:
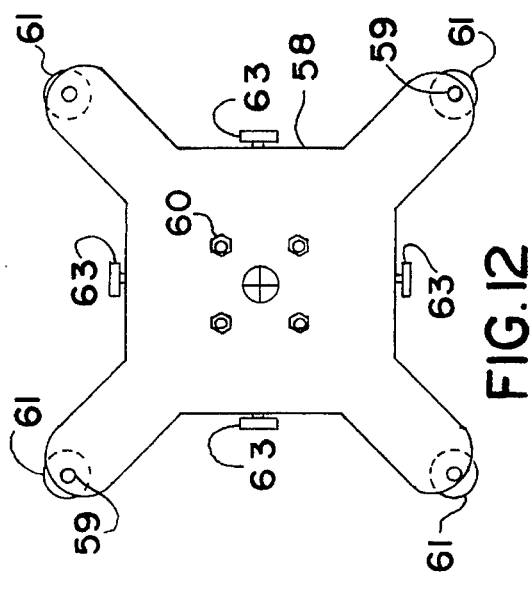
FIG. 12 is a perspective view of an annular disk plate attached to the underside of a drape according to the present invention.
Figure 10:
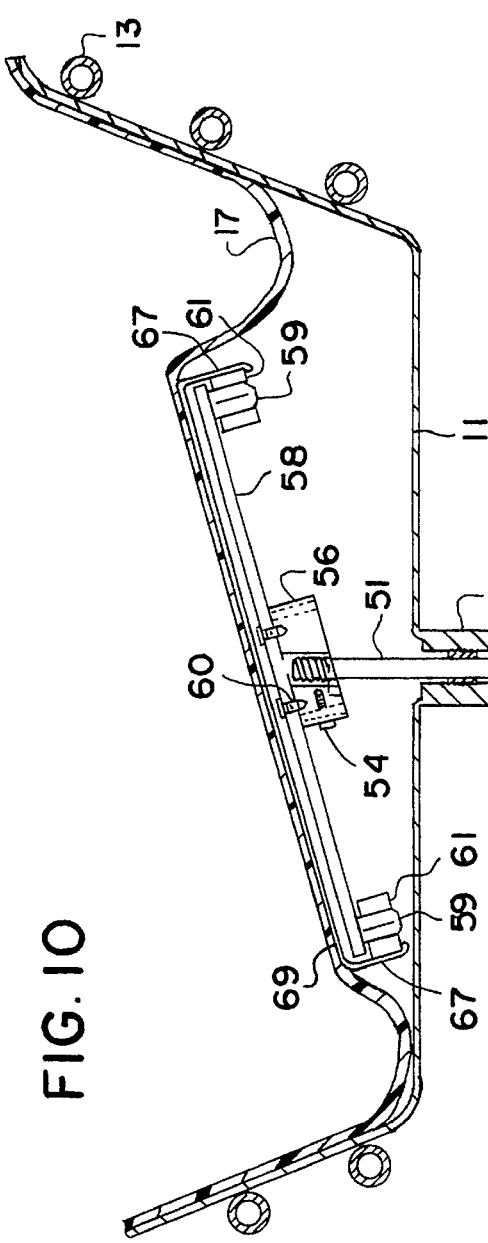
FIG. 10 is an elevational view in partial section of another embodiment of the present invention.
Figure 11:
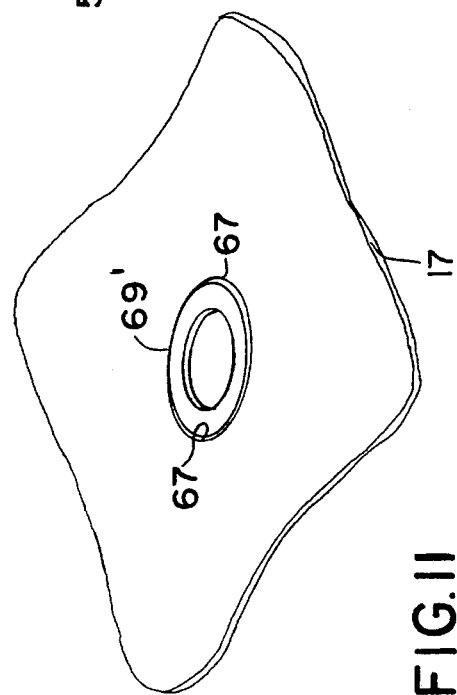
FIG. 11 is a top view in plan of a tilt plate variation on the embodiment of FIG. 10.

Although vertical reciprocation of the drape disk is the preferred embodiment of the present invention, it should be noted that other forms of drape disk movement, suitable for moving the sides of the drape container relative to the basin sides, are contemplated as being within the scope of the invention. Numerous examples of such types of motion are described and illustrated in the aforementioned U.S. Pat. No. 5,331,820. By way of one such example only, another such motion arrangement for the drape disk is illustrated in FIGS. 10–12 to which specific reference is now made. In this embodiment a wobble plate technique is utilized for dislodging frozen pieces of saline. Specifically, as with the embodiment described above, an adapter tube 53 includes an externally threaded bottom end engaged by a bracket 55 and a lock washer 57. Bracket 55 supports a gear motor assembly 50 within the machine cabinet and has a vertical drive shaft 51 arranged to rotate about its own longitudinal axis when driven by the motor. Drive shaft 51 extends upwardly through the adapter tube 53 to a location above the bottom wall of basin 11. The upper end of drive shaft 51 is secured by an angled set screw 54 through a tilt collar 56 to a tilted member or plate 58 having a diameter somewhat smaller than the diameter of the basin. Perpendicularly depending axle segments 59 extend downward from the perimeter of plate 58. Tilt collar 56 is secured to tilt plate 58 by threaded bolts 60. The axle segments carry respective freely rotatable wheels 61. Tilt plate 58 also has freely rotatable rollers 63, shown in FIG. 11, disposed intermediate the attachment location of shaft 51 and the perimeter of the plate. Tilt plate 58 is disposed at an angle on the order of 70° relative to shaft 51; the particular angle is not crucial but would typically be in the range of between 60° and 80°.

Wheels 61 are positioned to freely roll along the interior surface of an annular lip 67 depending from drape disk 69. The drape disk 69 is placed over tilt plate 58 and its wheels 61 prior to a surgical procedure. Annular lip 67 bends slightly inward at its lower edge to guide and retain wheels 61 and the bottom surface of disk 69 rests on rollers 63. By virtue of this arrangement, disk 69 is tilted relative to the basin bottom at the angle formed between plate 58 and the basin bottom. An alternative embodiment of drape disk 69', affixed to the underside of drape 17, need only interact smoothly with wheels 61 and can have an annular shape, as shown in FIG. 12 to minimize material cost and weight.

As drive shaft 51 is rotated by motor assembly 50, tilt plate 58 revolves, maintaining its tilted orientation, and causes wheels 61 to roll orbitally in a tilted annular path along annular lip 67. As the plate revolves relative to disk 69, different sections of the disk are successively raised and lowered, thereby resulting in a wobbling motion of the disk. As the disk cyclically wobbles, successive portions of drape 17 are pulled away from the basin sides, thereby causing frozen saline pieces to dislodge from the sides of the drape container and collect interiorly.

It will be noted that, in our U.S. Pat. No. 5,331,820, other types of disk motion are disclosed. For example, in FIGS. 2 and 3 of that patent, a horizontal disk is caused to cyclically rotate in opposite directions. This type of motion is suitable to the present invention wherein the disk is secured to the bottom of the drape container. Under such circumstances, the drape is alternately twisted in opposite directions to displace the drape container from the sides of the basin and remove any frozen saline pieces that have adhered to the drape.

It should be noted that the disk is preferably bonded to the underside of the drape container but could, for certain applications, be bonded to the top side of the drape. Likewise, although a disk or plate type configuration is preferred, any member capable of support slush and displacing the drape from the basin may be employed.

The present invention makes available a unique combination of a drape with a support permanently bonded thereto in a disposable assembly, the member being adapted to attach to a reciprocating or other movable mechanism in a surgical slush machine to cause the drape to be displaced from the sidewalls of the cooled basin.

Having described preferred embodiments of a new and improved sterile drape assembly for use in making surgical slush in accordance with the present invention, it is believed that other modifications, variations and changes will be suggested to persons skilled in the art in view of the teachings set forth herein. It is therefore to be understood that all such variations, modifications and changes are intended to fall within the scope of the present invention as defined by the appended claims.

We claim:

1. A surgical drape assembly for use as a sterile container of sterile medium in a surgical slush machine having a cooled basin recessed in the top surface of the machine, said machine including a longitudinally reciprocal vertically oriented shaft, said drape assembly comprising:

a sterile conformable sheet having a top side adapted to face away from said machine and an underside adapted to face said machine, said sheet being of sufficient size to cover and hang down from the top surface of said machine, said sheet having a container portion adapted to be substantially conformed to said basin; and a disk-like member secured to the underside of said container portion of said sheet, said disk-like member including a resilient lipped wall comprising a series of spaced wall increments configured to removably engage said disk-like member to said shaft.

2. A drape assembly for use with a surgical slush machine, said slush machine having a cooled basin recessed in the top surface of the machine, said machine includes a rotating shaft projecting vertically into said basin from below said basin, said drape assembly providing a sterile drape container conformable to said basin to contain sterile slush medium formed by the cooling of the basin, said drape assembly comprising:

a sheet of material having a top side and an underside, said sheet being impervious to said medium, said sheet being sized to overlie and hang down from said machine while forming a drape container substantially conformed to said cooling basin;

a disk-like member having a top surface and a bottom surface and having said top surface bonded to the underside of said sheet below said drape container, said disk-like member being sufficiently rigid to support said sterile medium without substantial bending or flexing;

support means for supporting said bottom surface of said disk-like member at an angle tilted with respect to said vertical rotating shaft; and means for attaching said tilted support means to said vertical rotating shaft.

3. The drape assembly of claim 2 further comprising freely rotatable rollers disposed between said support means and said disk-like member bottom surface.

4. The drape assembly of claim 2 wherein said support means is a plate extending radially in at least one direction to the edge of said disk-like member.

5. The drape assembly of claim 4 further comprising an annular lip extending from said disk-like member bottom surface and wheels attached to said support plate disposed to freely rotate in said annular lip.

6. The drape assembly of claim 5 wherein said support plate comprises a plurality of radially extending equally angularly spaced arms, each of said arms having a wheel attached thereto, said wheels freely rotatable in said annular lip.

7. The drape assembly of claim 6 having four equally spaced arms.

8. The drape assembly of claim 7 further comprising four equally spaced freely rotatable rollers disposed between said support plate and said disk-like member bottom surface.

9. The drape assembly of claim 2 wherein said attachment means comprises an annular collar attached to said support means and fastened to said vertical shaft by an angled set-screw.

10. The drape assembly of claim 2 wherein said disk-like member has an annular shape.

* * * * *